(12) United States Patent
Kohli et al.

(10) Patent No.: US 9,272,093 B2
(45) Date of Patent: Mar. 1, 2016

(54) DUAL DRUG PEN-INJECTION DEVICE WITH MICRO-RESERVOIRS CARRYING SECONDARY DRUG FOR EMERGENCY INJECTION

(75) Inventors: Amit Kohli, Paris (FR); Christian Lerche, Paris (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 138 days.

(21) Appl. No.: 13/981,543

(22) PCT Filed: Feb. 8, 2012

(86) PCT No.: PCT/EP2012/052136
§ 371 (c)(1),
(2), (4) Date: Jul. 24, 2013

(87) PCT Pub. No.: WO2012/107493
PCT Pub. Date: Aug. 16, 2012

(65) Prior Publication Data
US 2013/0324920 A1   Dec. 5, 2013

Related U.S. Application Data

(60) Provisional application No. 61/441,266, filed on Feb. 9, 2011.

(51) Int. Cl.
*A61M 37/00*   (2006.01)
*A61M 5/19*   (2006.01)
*A61M 5/00*   (2006.01)
(Continued)

(52) U.S. Cl.
CPC ............... *A61M 5/19* (2013.01); *A61M 5/003* (2013.01); *A61M 5/2448* (2013.01); *A61M 5/31* (2013.01); *A61K 38/00* (2013.01); *A61K 38/26* (2013.01); *A61K 38/28* (2013.01); *A61M 2037/0023* (2013.01); *A61M 2205/0244* (2013.01); *A61M 2205/581* (2013.01); *A61M 2205/583* (2013.01);
(Continued)

(58) Field of Classification Search
CPC ...... A61M 5/178; A61M 5/2448; A61M 5/14; A61M 5/31; A61M 5/16827; A61M 2205/50; A61M 5/31525; A61M 5/20; A61M 2005/1787; A61M 5/19; A61M 5/00; A61M 3/00; A61M 2037/0023; A61M 37/0015; A61M 5/3294; A61M 5/31536
See application file for complete search history.

(56) References Cited

U.S. PATENT DOCUMENTS 5,183,467 A * 2/1993 Mouney ..................... 604/149
5,417,667 A * 5/1995 Tennican et al. ........... 604/191
(Continued)

FOREIGN PATENT DOCUMENTS

WO    2004078239 A1    9/2004
WO    2006014426 A1    2/2006
(Continued)

*Primary Examiner* — Nathan R Price
*Assistant Examiner* — Morgan Lee
(74) *Attorney, Agent, or Firm* — McDonnell Boehnen Hulbert & Berghoff LLP

(57) ABSTRACT

An injection device to deliver at least two medicaments is disclosed where a first medicament is delivered in settable doses with a first medicament dose delivery mechanism and a second medicament is delivered from micro-reservoirs upon activation of a second medicament delivery system, whereby activation of the second medicament delivery system locks out the first medicament dose delivery mechanism.

20 Claims, 3 Drawing Sheets

(51) Int. Cl.
  *A61M 5/24* (2006.01)
  *A61M 5/31* (2006.01)
  *A61K 38/00* (2006.01)
  *A61K 38/26* (2006.01)
  *A61K 38/28* (2006.01)
  *G06F 19/00* (2011.01)

(52) U.S. Cl.
  CPC .... *A61M 2205/8206* (2013.01); *G06F 19/3468* (2013.01)

(56) References Cited

U.S. PATENT DOCUMENTS

| | | |
|---|---|---|
| 6,572,542 B1 | 6/2003 | Houben et al. |
| 7,497,846 B2 | 3/2009 | Uhland et al. |
| 7,648,483 B2 * | 1/2010 | Edwards et al. .............. 604/140 |
| 2004/0087893 A1 | 5/2004 | Kwon |
| 2005/0277912 A1 * | 12/2005 | John .......................... 604/890.1 |
| 2008/0306436 A1 * | 12/2008 | Edwards et al. .............. 604/140 |
| 2008/0312604 A1 * | 12/2008 | Boesen ......................... 604/207 |
| 2009/0240232 A1 * | 9/2009 | Gonnelli et al. .............. 604/506 |

FOREIGN PATENT DOCUMENTS

| | | |
|---|---|---|
| WO | 2010139676 A1 | 12/2010 |
| WO | 2010149734 A1 | 12/2010 |

\* cited by examiner

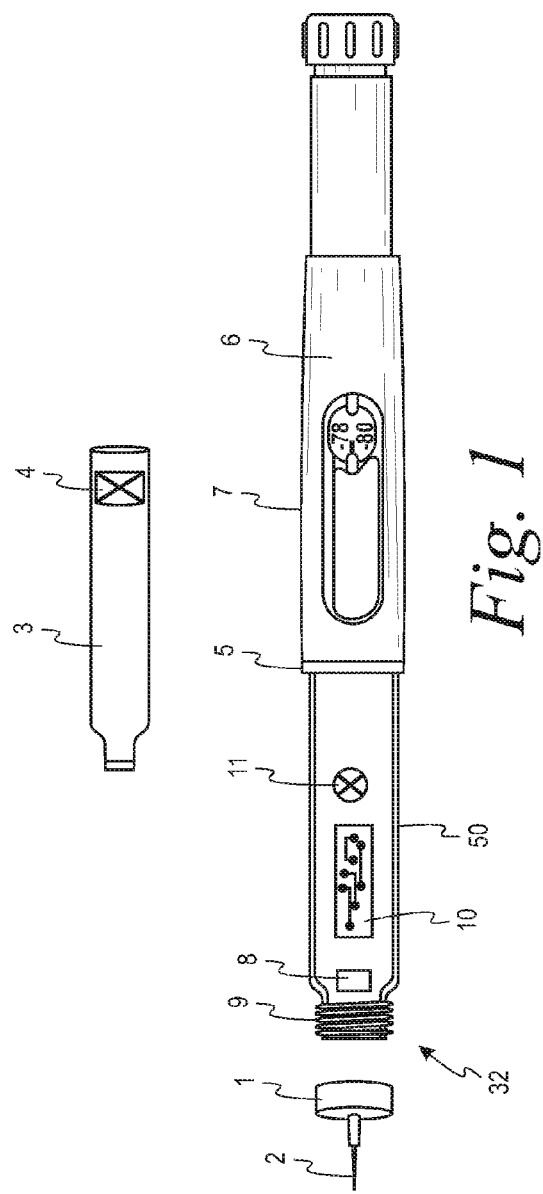
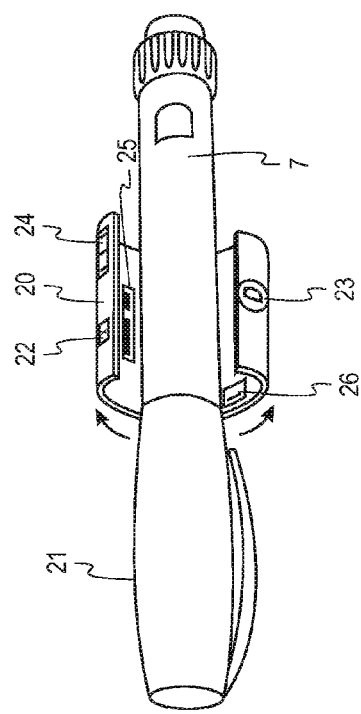
Fig. 1
Fig. 2

DUAL DRUG PEN-INJECTION DEVICE WITH MICRO-RESERVOIRS CARRYING SECONDARY DRUG FOR EMERGENCY INJECTION

CROSS REFERENCE TO RELATED APPLICATIONS

The present application is a U.S. National Phase Application pursuant to 35 U.S.C. §371 of International Application No. PCT/EP2012/052136 filed Feb. 8, 2012, which claims priority to U.S. Provisional Patent Application No. 61/441,266 filed Feb. 9, 2011. The entire disclosure contents of these applications are herewith incorporated by reference into the present application.

FIELD OF INVENTION

This invention relates to medical devices and methods of delivering multiple doses of a first medicament and predetermined, non-user-settable dose of a second medicament from a single injection device, preferably a pen-type injection device. The second medicament is administered from micro-reservoirs and can use a single dispense interface common to the container holding the first medicament. Our invention can include electronics that control the administration of the second medicament, provides visual and verbal instructions to the user, and/or can initiate a mechanical lockout of the first medicament dose delivery mechanism to prevent further use of the injection device.

BACKGROUND

There are some disease states where a patient needs to constantly administer a medicament to keep the disease in check. Typically the medicament is delivered by injection, infusion or inhalation one or more times a day. There is always the risk that a patient will accidentally overdose the medicament or suffer some physiologic incident that requires the administration of a second medicament to correct the problem. For example, people suffering from diabetes typically inject themselves with insulin to control their blood sugar. Insulin is a hormone that reduces blood sugar and is normally produced by the pancreas in response to increased glucose levels in the blood.

Hypoglycemia is a condition that is relatively common in persons with diabetes and occurs when the blood sugar (glucose) is too low, typically below 70 mg/dL. Hypoglycemia occurs when the blood sugar (glucose) is used up too quickly, or glucose is released into the bloodstream too slowly, or too much insulin is released into the bloodstream. Another hormone, glucagon, can be used to counteract hypoglycemia by producing the opposite effects to those of insulin, including, primarily, increasing hepatic glucose output and thereby increasing blood glucose levels. Glucagon levels tend to increase when blood glucose levels fall to abnormally low levels, particularly in patients who utilize insulin injections.

Current goals for diabetes management include near normal blood glucose levels to delay or prevent microvascular complications; achievement of this goal usually requires intensive insulin therapy. In striving to achieve this goal, physicians have encountered a substantial increase in the frequency and severity of hypoglycemia in their diabetic patients. Frequent recurrent bouts of hypoglycemia can be associated with hypoglycemic unawareness that can further contribute to development of hypoglycemia, which is sometimes severe. Thus, efforts to achieve normal glucose levels with insulin can result in the development of hypoglycemia of varying frequency and severity in patients. Hypoglycemia and the lack of awareness of its presence are serious complications of insulin therapy that occur with greater frequency and severity when impaired counter-regulatory (anti-insulin) responses are present in diabetic patients.

One of the major counter-regulatory hormones that normally responds to hypoglycemia is glucagon. An injectable form of glucagon is available as a prescription emergency kit, for use to treat severe insulin reactions. The glucagon is injected and raises blood glucose levels within a half-hour. It is frequently recommended that people with Type 1 diabetes, and other people taking insulin injections, have a family member learn how to administer glucagon. Within the emergency glucagon kit are a syringe pre-filled with a liquid and a separate vial of powdered glucagon. The instructions for the kit require that the glucagon must be prepared for injection immediately before use by following a very specific reconstitution procedure to solubilize the powdered glucagon so it can be injected.

Unfortunately, these known glucagon emergency kits require a manually dexterous "operator" or "user" who is composed, confident and competent in the whole procedure. Since an insulin user usually needs administration of glucagon during seizures and/or unconsciousness they obviously must rely on others to assist them in such emergencies. However, despite public relations to increase the awareness of the life saving capability of glucagon rescue, it is still largely unknown by the general public. Indeed, studies have shown that parents of diabetic children had significant problems with glucagon emergency kits, including handling difficulties ranging from opening the container to drawing the correct dose into the syringe. Clearly, there is a need in the art to have a simplified or "fool proof" system and method for administrating glucagon by both the diabetic and in extreme hypoglycemic reactions by another person, preferably in a single injection or delivery step that is simple for the user to perform.

Our invention overcomes the above-mentioned problems by providing a single injection device that is used to inject multiple doses of a first medicament, such as insulin to treat diabetes, but also contains one or more preset doses of second medicament, such as glucagon, that can be administered to treat or prevent an adverse event, such as a hyperglycemic event. Preferably, our device would include electronics, microprocessors that would provide the user with visual and/or audio prompts to assist the user in administering the second medicament. Additionally, the injection device would have an automatic lockout feature to prevent the device from further administration of the first medicament.

These and other advantages will become evident from the following more detailed description of the invention.

SUMMARY

Our invention relates to a device and method where a first medicament delivery system is configured to allow a user to set and deliver multiple doses of a first medicament contained in a cartridge. The device contains micro-reservoirs of a second medicament coupled to a separate delivery system that is independent of the delivery system coupled to the cartridge containing the first medicament. Preferably, the second delivery system is automated in that it does not allow the user of the device to set or change the predetermined dose of the second medicament. In other words, once the second delivery system is activated, such as in an emergency situation, the amount of the second medicament administered cannot be varied by the user and the administration will proceed without further input from the user.

In one preferred embodiment our invention covers a drug delivery device, comprising a multi-dose cartridge containing a first medicament. This cartridge is coupled to a first medicament dose delivery mechanism configured to allow a user to set and administer multiple doses of the first medicament through a dispense interface. The drug delivery device also has a plurality of micro-reservoirs of a second medicament that is couple to a second medicament delivery system configured to deliver a preset dose of the second medicament through the dispense interface or through a separate dispense interface, both of which are preferably needle cannula. The first dose delivery mechanism that sets and delivers doses of the first medicament is preferably a conventional mechanical dose setting mechanism typically found on pen-type injection devices, particularly those for the delivery of insulin or human growth hormone. The second medicament delivery system is preferably one that incorporates microchip technology, specifically where one or more microchips contain micro-reservoirs and can be controlled by a microprocessor to deliver a preset or predetermined dose of the second medicament. In some instances, it may be necessary for the second medicament delivery system to include a means to formulate the second medicament, for example through a reconstitution step where a dry drug compound, for example where lyophilized dry powder glucagon is mixed with a liquid excipient or diluent, for example sterile water, to arrive at the formulated second medicament.

Microchip technology is based on reservoir arrays (i.e., micro-reservoirs) that are used to store and protect the second medicament in the microchip for long periods of time. Examples of the types of reservoir arrays that can be used in our invention are described in U.S. Pat. No. 7,497,846. The '846 patent describes the structure and functionality of miniaturized devices for the controlled release of substances that are hermetically sealed in a plurality of micro-reservoirs. The full description of such microchip devices is disclosed in the '846 patent, which is incorporated herein by reference. The microchip arrays are designed for compatibility with preprogrammed microprocessors, wireless telemetry, or sensor feedback loops to provide active control. Individual device reservoirs can be opened on demand or on a predetermined schedule to precisely control drug release. Microchips can be made of silicon, each the size of a postage stamp and can contain a plurality of tiny "wells" or "micro-reservoirs." Each reservoir is filled with the second medicament and capped with an electrically-erodable membrane, preferably made of platinum and titanium. Filled chips are then incorporated into the injection device, preferably during manufacture, are sealed and connected to an electronic hardware also located in the injection device, such as power, and wireless connectivity. One or more microprocessors on the injection device and/or external to the injection device run the software that controls operation of the microchip. Wireless devices can also be used to activate the microchips or to program the device, for example to modify the preset dose of the second medicament. The microchip can be programmed to release one or more the multiple micro-reservoirs contained in the chip to achieve the desired dose. Of course, in those situations where the drug must be formulated through reconstitution for example, one or more of the reservoirs can contain the dry form of the drug and other reservoirs could contain the diluent. Or alternatively, a separate container of liquid excipient could use to supply the necessary liquid to the reservoirs containing the dry drug. Vibration, sonic waves, heat or other means can be used to insure the diluent and the drug are correctly formulated before being administered to the patient.

The location on the injection device of the microchip containing the second medicament is not critical to our invention, however, it should be positioned on the injection device in a convenient location such that the second medicament could be expelled through the same dispense interface utilized to expel the first medicament. In some instances it will be possible to expel the second medicament through a dispense interface dedicated to the microchip, for example through a plurality of micro needles associated with the reservoirs of secondary medicament on the chip. This second dispense interface would not be in fluid connection with the first medicament. In these circumstances, it may be desirable to locate the microchip at or near the outside surface of the housing of the injection device so that the user can apply the second dispense interface directly to an injection site. In those circumstances where the injection device has only a single dispense interface in fluid communication with the first medicament, then a system of conduits can be used to connect the microchip of the second drug delivery system to the dispense interface, possibly utilizing one way check valves or other flow controls to allow the second medicament to be dispensed through the single dispense interface, preferably a needle cannula, without mixing or interaction with the first medicament.

The drug device of our invention could also contain a feature whereby the activation of the second medicament delivery system locks out the first dose delivery mechanism preventing further dose setting and administration of the first medicament. This can be a very important safety feature and may be necessary from a regulatory perspective. This lock out feature can be an electromechanical mechanism triggered by the electronics or microprocessor associated with the microchip in the second medicament delivery system or in combination with another electronic circuit system that can be used to activate audio instructions to assist the user in administering the second medicament. The lockout feature could physically disable the injection device such that a dose of the first medicament could not be set and/or to prevent the injection of a set dose.

In another possible configuration the drug delivery device may contain one or more electronic circuit systems coupled to the second medicament delivery system configured to output a plurality of electronic outputs instructing a user of the drug delivery device on how to administer a dose of the second medicament. This would be beneficial in an emergency situation where the patient is incapacitated and another person who is inexperienced with giving injections must administer the second medicament in response to an adverse event. This user notification system could take the form of a microprocessor incorporated into the internal portion of the drug delivery device or alternatively, it could be incorporated in an external circuitry configuration that is applied to the outside of the housing, say for example, as part of wrap around label. Preferably, the notification system combines both audio and visual instruction to a user providing step-by-step instructions for how to operate and administer the preset dose of the second medicament.

The drug delivery device of present invention could also have an electronic circuit system coupled to the second medicament delivery system configured to transmit or receiver a signal indicating that the second medicament delivery system was activated and that the preset dose of second medicament was delivered. The electronic circuit could also be configured to be programmable through a wireless connection.

Although any number of drugs could be used as the first and second medicaments, one preferred system would have the first the first medicament comprise insulin and the second medicament comprise glucagon-containing solution. The glucagon solution could be formulated by the second medicament delivery system through reconstitution of dry glucagon and a liquid excipient or diluent. Such a drug delivery system allows administration of insulin from a multi-dose container or cartridge to a diabetic patient while also allowing an emergency administration of glucagon to prevent or treat a hyperglycemic condition. This would eliminate the need for a separate glucagon emergency kit and would eliminate the need for the user to manually perform a reconstitution procedure followed by a manual injection. In an emergency situation our invention is of particular benefit to users with dexterity or computational difficulties as second medicament delivery system automates the delivery of the second medicament and removes the need for the user to calculate doses or perform the reconstitution step.

Although our invention specifically mentions insulin, insulin analogs or insulin derivatives, and glucagon, a number of other combinations could be employed for example insulin and GLP-1 or GLP-1 analogs or possible drug combinations, such as an analgesics, hormones, beta agonists or corticosteroids, or a combination of any of the above-mentioned drugs.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Any form of glucagon can be used in our invention including that extracted form beef and pork pancreas. Preferably, the glucagon is one produced by the expression of recombinant DNA and that has a chemical structure identical to naturally occurring human glucagon with an empirical formula of $C_{153}H_{225}N_{43}O_{49}S$, a molecular weight of 3483, and a single-chain polypeptide containing 29 amino acids residues. Preferably, the glucagon used in our invention is supplied as a sterile, lyophilized white powder and is accompanied in a separate container with sterile water for reconstitution.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In a preferred embodiment of our invention, the drug delivery device is used more than once and therefore is multi-use; however, the drug delivery device may also be a single use disposable device. Such a device may or may not have a replaceable reservoir of the first medicament, but our invention is equally applicable to both scenarios. As mentioned our invention includes the lockout feature that will deactivate the first medicament dose delivery mechanism once the second medicament delivery system has been activated. The injection device would have a means to alert the patient to this situation and the inability to use the device to administer the first medicament. Visual warnings (e.g. change in color and/or warning text/indicia within an indication window on the housing of the device) can also be used. Additionally, tactile feedback (presence or absence of tactile features on the outer surface of the module hub following use) could be used as well. And of course, audio warnings could be incorporated in the electronic circuits and/or microprocessor associated with the second medicament delivery system.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates one possible drug delivery device that can be used with the present invention;

FIG. 2 illustrates an alternative drug delivery device for use with our invention;

DETAILED DESCRIPTION

Figure 3:
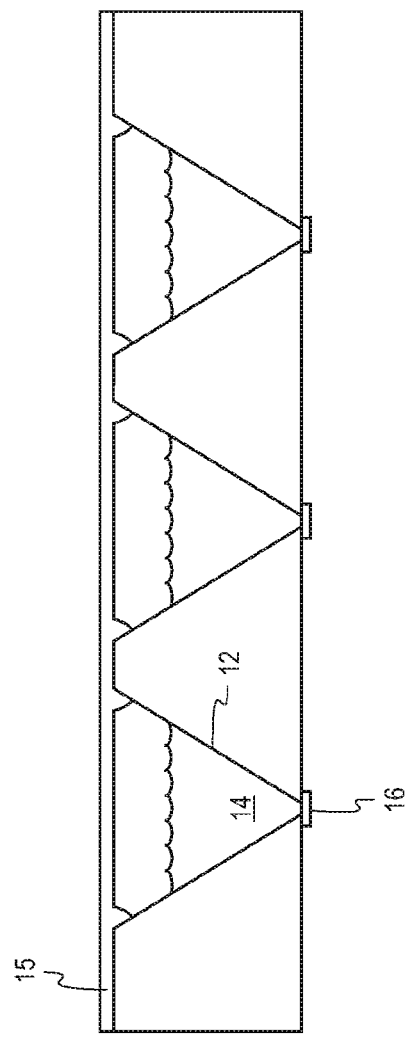
FIG. 3 illustrates one possible microchip that can be used in our invention.
Figure 3:
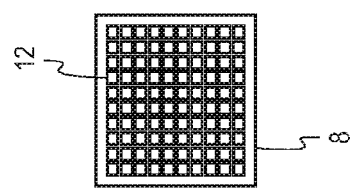

The present invention administers a fixed predetermined dose of a second medicament and a variable dose of a first medicament, preferably, but not necessarily through a single output or drug dispense interface. Setting the dose of the first medicament by the user is preferably accomplished through a mechanical dose setting and dose delivery mechanism that is completely independent and separate from the dose delivery system used to deliver the second medicament. The only commonality would be the dispense interface in those embodiments where there is not a separate dispense interface dedicated to the second medicament and the second medicament delivery system. The preferred dispense interface is a needle cannula. Acceptable first medicament dose delivery mechanisms for use in our invention would include those found on pen-type injection devices, particular those that are described in published patent application WO 2004/078239. The '239 application describes the structure and functionality of drive mechanisms of the pen-type injection devices, specifically the interaction of a drive sleeve, a clutch means, a dose dial sleeve, a housing and a piston rod during both dose setting and dose delivery. The full description of the pen-type injection devices disclosed in WO 2004/078239 is incorporated herein by reference.

FIG. 1 illustrates one example of a drug delivery device 7 that can be used in our invention illustrated as a pen-type multi-dose injection device. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge 3 having a movable piston 4 or other container that contains the first medicament. This cartridge is typically cylindrical in shape and is usually manufactured in glass. The cartridge is sealed at one end with the piston or rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle, lead screw or piston rod (not shown) that engages the piston 4 in cartridge 3 to force the set dose of first medicament out the dispense interface. In a further embodiment the spindle is a rotatable piston rod comprising two distinct threads.

A connection means 5 allows cartridge holder 50 to be connected to first medicament dose delivery mechanism 6. Cartridge holder 50 accepts cartridge 3. Distal connection means 9 on the distal end 32 of cartridge holder 50 accepts pen needle 1 that has mounted a needle cannula 2, preferably a double-ended cannula that is configured to pierce the septum at the distal end of cartridge 3. Although not shown, the injection device shown in FIG. 1 could be supplied by a manufacturer in a protective and sterile container, where the user would peel or rip open a seal or the container itself to gain access to the sterile injection device. Any known attachment or connection means 5 and 9 can be used to attach the cartridge holder to the dose delivery mechanism 6 and to the pen needle 1, respectively, including all types of permanent and removable connection means, such as threads, snap locks, snap fits, luer locks, bayonet, snap rings, keyed slots, and combinations of such connections.

FIG. 2 illustrates the injection device 7 having in place protective cap 21 covering the cartridge holder 50. The injection device 7 can include an electronic circuit system 20 configured to provide a predetermined sequence of electronic outputs and/or electronic signals during the use of the injection device. The electronic circuit system 20 is powered by a battery 24 and includes a processor 25, a start button 22, switches, visual output devices (not shown), an audio output device 23, and a network interface device 26. The components of the electronic circuit system 20 are operatively coupled by any suitable mechanism, such as, for example, a printed circuit board (not shown) having conductive traces.

When it is desired or necessary to administer the second medicament, the start button 22 can be manually actuated by the user to begin the sequence of electronic outputs and to trigger a lock out of the first medicament dose delivery mechanism 6. The electronic circuit system 20 can produce and/or output an electronic signal and/or an electronic output when the start button 22 is pushed. Proximity sensors (not shown) can be disposed on the injection device and configured to produce an output when the device engages the body. The proximity sensor can be, for example, a temperature sensor, an optical sensor, pressure sensor, impedance sensor or the like. In this manner, the processor can be prompted to output a predetermined electronic output when the injection device is positioned against the body.

In some embodiments, the electronic circuit system 20 can be configured to activate visual output devices (not shown) that are in electronic communication with the processor and are configured to produce an output in response to an electronic signal output by the processor. The visual output devices can be any suitable visual indicia, such as, light-emitting diodes (LEDs), liquid-crystal display (LCD) screens, optical polymers, fiber optic components or the like. The audio output device 23 is disposed such that it can project sound outside of the injection device. The audio output device 23, as well as any other audio output devices referenced herein, can be any suitable device for producing sound, such as a micro-speaker a piezo-electric transducer or the like. Such sound output can include, for example, an alarm, a series of beeps, recorded speech or the like. The audio output device 23 is in electronic communication with the processor 25 and is configured to produce an output in response to an electronic signal output by the processor.

Figure 4:
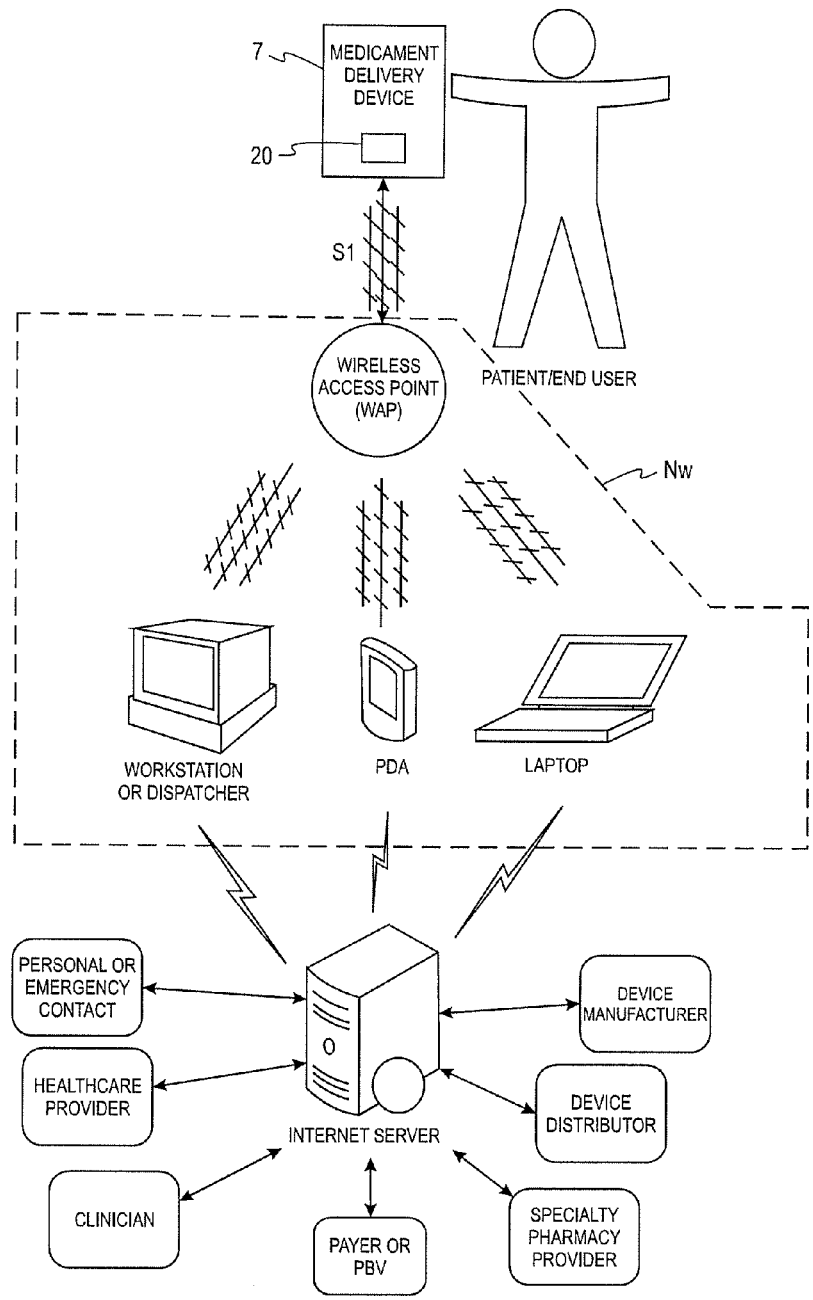
FIG. 4 illustrates possible communication means between the drug delivery device our invention and various other computer based devices.

The network interface device 26 is configured to operatively connect the electronic circuit system 20 to a remote devices and/or communications networks (see FIG. 4). In this manner, the electronic circuit system 20 can send information to and/or receive information from the remote devices or networks. The remote devices can be, for example, a remote communications network, a computer, a compliance monitoring device, a cell phone, a personal digital assistant (PDA) or the like. Such an arrangement can be used, for example, to download replacement processor-readable code to the electronic circuit 20 and/or the electronic circuit 10 from a central network. In some embodiments, for example, the electronic circuit system 20 can download information associated with the first medicament or second medicament, such as an expiration date, a recall notice, updated use and/or dose instructions, or the like. Similarly, in some embodiments, the electronic circuit system 20 can upload changes to the predetermined dose that can be delivered by the second medicament delivery system via the network interface device.

FIG. 1 illustrates one possible location of the second medicament delivery system comprising a combination of a microchip 8 coupled to an electronic circuit 10 that preferably contains a microprocessor. A trigger 11 can be user accessible to activate the second medicament delivery system to deliver the preset dose of the second medicament. FIG. 3 illustrates one possible microchip design 8 comprising a plurality of tiny micro-reservoirs 12. As the side view of the microchip illustrates, each of the reservoirs 12 is capped with a sealing layer 15 and can contain a predetermined amount the second medicament 14. Each reservoir also may have a dedicated outlet port 16. Manifolds and other conduits are not shown for clarity, but are known to those skilled in the art and could be used in combination with the microprocessor to combine the individual quantities of the second medicament from two or more reservoirs 12 to produce a desired predetermined dose. This system of conduits would connect to the needle cannula 2 through an appropriate system valve so that only a single dispense interface is needed for the injection device 7.

Alternatively, the microchip could have a system of dedicated micro needles associated exclusively with the chip to provide a second dispense interface that would deliver the second medicament directly to the patient and not use the dispense interface connected to the cartridge containing the first medicament. It is highly desirable that the microchip be configured as small as possible so that it dose not significantly change the overall dimensions of a typical pen-type injection device. Preferably the microchip reservoirs, flow distributors, valves and conduits be made from materials that are compatible with the second medicament. Examples of compatible materials of construction include, but are not limited to, COC (an amorphous polymer based on ethylene and norbornene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with cartridge 3 can be manufactured using TPE (thermo plastic elastomer); LSR (liquid silicone rubber); LDPE (low density polyethylene); and/or any kind of medical grade rubber, natural or synthetic.

One possible feature of our medicated module assembly is the inclusion of user feedback that is given when the assembly is used. In particular, the microprocessor controlling the dispense of the second medicament from the microchip will interface with the electronic circuit system 20 to provide the user and persons remotely with signals or other outputs that confirm the second medicament was successfully administered.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery device, comprising,
a cartridge of a first medicament;
a first medicament dose delivery mechanism configured for user settable administration of multiple doses of the first medicament through a dispense interface;
a plurality of micro-reservoirs of a second medicament; and
a second medicament delivery system configured to deliver a preset dose of the second medicament through a second dispense interface, the second medicament delivery system comprising a lock out feature,
wherein activation of the lock out feature of the second medicament delivery system locks out to physically disable the first dose delivery mechanism preventing
both dose setting and dose administration of the first medicament.

2. The drug delivery device of claim 1 where the second medicament delivery system comprises a microchip coupled to a microprocessor for controlling delivery of the preset dose.

3. The drug delivery device of claim 1 where the dispense interface is a needle cannula.

4. The drug delivery device of claim 1 further comprising an electronic circuit system coupled to the second medicament delivery system configured to output a plurality of electronic outputs instructing a user of the drug delivery device on how to administer a dose of the second medicament.

5. The drug delivery device of claim 1 further comprising an electronic circuit system coupled to the second medicament delivery system configured to transmit to a receiver, a signal indicating activation of the second medicament delivery system.

6. The drug delivery device of claim 1 where the drug delivery device is configured as a pen-type injection device.

7. The drug delivery device of claim 1 where the second medicament delivery system comprises an electromechanical microchip configured to formulate the second medicament through a reconstitution step and subsequently deliver a non-user settable dose of the second medicament through a needle cannula.

8. The drug delivery device of claim 1 where the second medicament delivery system is programmable through a wireless connection.

9. The drug delivery device of claim 1 where the first medicament is insulin and the second medicament is glucagon solution.

10. The drug delivery device of claim 9 where the glucagon solution is formulated by the second medicament delivery system through reconstitution of lyophilized glucagon and a liquid excipient.

11. A drug delivery device, comprising,
a cartridge of a first medicament;
a first medicament dose delivery mechanism configured for user settable administration of multiple doses of the first medicament through a dispense interface;
a plurality of micro-reservoirs of a second medicament; and
a second medicament delivery system configured to deliver a preset dose of the second medicament through a second dispense interface, the second medicament delivery system comprising a lock out feature,
wherein activation of the lock out feature of the second medicament delivery system locks out to physically disable the first dose delivery mechanism preventing
both dose setting and dose administration of the first medicament
wherein the lock out feature comprises an electromechanical triggering mechanism.

12. The drug delivery device of claim 11 where the second medicament delivery system comprises a microchip coupled to a microprocessor for controlling delivery of the preset dose.

13. The drug delivery device of claim 11 where the dispense interface is a needle cannula.

14. The drug delivery device of claim 11 further comprising an electronic circuit system coupled to the second medicament delivery system configured to output a plurality of electronic outputs instructing a user of the drug delivery device on how to administer a dose of the second medicament.

15. The drug delivery device of claim 11 further comprising an electronic circuit system coupled to the second medicament delivery system configured to transmit to a receiver, a signal indicating activation of the second medicament delivery system.

16. The drug delivery device of claim 11 where the drug delivery device is configured as a pen-type injection device.

17. The drug delivery device of claim 11 where the second medicament delivery system comprises an electromechanical microchip configured to formulate the second medicament through a reconstitution step and subsequently deliver a non-user settable dose of the second medicament through a needle cannula.

18. The drug delivery device of claim 11 where the second medicament delivery system is programmable through a wireless connection.

19. The drug delivery device of claim 11 where the first medicament is insulin and the second medicament is glucagon solution.

20. The drug delivery device of claim 19 where the glucagon solution is formulated by the second medicament delivery system through reconstitution of lyophilized glucagon and a liquid excipient.

* * * * *